(12) United States Patent  (10) Patent No.: US 8,137,344 B2
Jia et al.  (45) Date of Patent: Mar. 20, 2012

(54) FLEXIBLE, AUTOMATED CAPSULORHEXIS DEVICE

(75) Inventors: Guangyao Jia, Irvine, CA (US); Daniel J. Kao, Lake Forest, CA (US); Glenn Sussman, Laguna Nigel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 617 days.

(21) Appl. No.: 12/331,800

(22) Filed: Dec. 10, 2008

(65) Prior Publication Data

US 2010/0145447 A1   Jun. 10, 2010

(51) Int. Cl.
A61B 18/14 (2006.01)
(52) U.S. Cl. ............................................. 606/45; 606/48
(58) Field of Classification Search .................. 606/28, 606/29; 607/99; 600/383
See application file for complete search history.

(56) References Cited

U.S. PATENT DOCUMENTS

| | | |
|---|---|---|
| 3,159,161 A | 12/1964 | Ness |
| 3,809,093 A | 5/1974 | Abraham |
| 3,844,272 A | 10/1974 | Banko |
| 3,915,172 A | 10/1975 | Wichterle et al. |
| 3,949,750 A | 4/1976 | Freeman |
| 4,002,169 A | 1/1977 | Cupler, II |
| 4,026,295 A | 5/1977 | Lieberman |
| 4,068,664 A | 1/1978 | Sharp et al. |
| 4,210,146 A | 7/1980 | Banko |
| 4,301,802 A | 11/1981 | Poler |
| 4,367,744 A | 1/1983 | Sole |
| 4,368,734 A | 1/1983 | Banko |
| 4,457,757 A | 7/1984 | Molteno |
| 4,481,948 A | 11/1984 | Sole |
| 4,501,274 A | 2/1985 | Skjaerpe |
| 4,530,356 A | 7/1985 | Helfgott et al. |
| 4,530,359 A | 7/1985 | Helfgott et al. |
| 4,531,934 A | 7/1985 | Kossovsky et al. |
| 4,559,942 A | 12/1985 | Eisenberg |
| 4,570,632 A | 2/1986 | Woods |
| 4,607,622 A | 8/1986 | Fritch et al. |
| 4,676,243 A | 6/1987 | Clayman |
| 4,706,669 A | 11/1987 | Schlegel |

(Continued)

FOREIGN PATENT DOCUMENTS

DE  3038024 A1  4/1982

(Continued)

OTHER PUBLICATIONS

Bretton, Randolph H. et al., "Use of bipolar diathermy to prevent posterior capsule opacification," Journal of Cataract Refractive Surgery 2002; 2 8:866-878.

(Continued)

*Primary Examiner* — Michael Peffley
*Assistant Examiner* — Thomas Giuliani

(57) ABSTRACT

A capsularhexis electrode device and corresponding insertion tool are disclosed. A flexible capsulorhexis electrode device comprises an elastomeric ring, first and second electrically conductive traces disposed at a first face of the elastomeric ring and extending concentrically around the elastomeric ring, and first and second electrically conductive connectors. The first and second electrically conductive connectors are electrically connected to the first and second traces, respectively, and are disposed at opposing points across the elastomeric ring from one another. An insertion tool includes first and second stretcher bars with connectors for mating to the electrode device. One of the stretcher bars translates relative to the other to elongate the flexible electrode device for insertion into the anterior chamber of the eye through a small incision.

14 Claims, 5 Drawing Sheets

U.S. PATENT DOCUMENTS

| | | | |
|---|---|---|---|
| 4,708,138 A | 11/1987 | Pazandak | |
| 4,729,761 A | 3/1988 | White | |
| 4,765,331 A * | 8/1988 | Petruzzi et al. | 606/50 |
| 4,766,896 A | 8/1988 | Pao | |
| 4,766,897 A | 8/1988 | Smirmaul | |
| 4,781,675 A | 11/1988 | White | |
| 4,805,616 A | 2/1989 | Pao | |
| 4,869,716 A | 9/1989 | Smirmaul | |
| 4,885,004 A | 12/1989 | Pao | |
| 4,900,300 A | 2/1990 | Lee | |
| 4,911,161 A | 3/1990 | Schechter | |
| 4,936,825 A | 6/1990 | Ungerleider | |
| 4,950,272 A | 8/1990 | Smirmaul | |
| 4,955,859 A | 9/1990 | Zilber | |
| 4,955,894 A | 9/1990 | Herman | |
| 4,986,825 A | 1/1991 | Bays et al. | |
| 4,994,066 A | 2/1991 | Voss | |
| 5,047,008 A | 9/1991 | de Juan, Jr. et al. | |
| 5,085,664 A | 2/1992 | Bozzo | |
| 5,123,906 A | 6/1992 | Kelman | |
| 5,135,530 A * | 8/1992 | Lehmer | 606/107 |
| 5,180,362 A | 1/1993 | Worst | |
| 5,188,634 A | 2/1993 | Hussein et al. | |
| 5,199,445 A | 4/1993 | Rubinfeld | |
| 5,203,865 A | 4/1993 | Siepser | |
| 5,234,436 A | 8/1993 | Eaton et al. | |
| 5,242,404 A | 9/1993 | Conley et al. | |
| 5,242,449 A | 9/1993 | Zaleski | |
| 5,261,923 A | 11/1993 | Soares | |
| 5,269,787 A | 12/1993 | Cozean, Jr. et al. | |
| 5,322,504 A | 6/1994 | Doherty et al. | |
| 5,342,377 A | 8/1994 | Laszerson | |
| 5,346,491 A | 9/1994 | Oertli | |
| 5,360,399 A | 11/1994 | Stegmann | |
| 5,364,405 A | 11/1994 | Zaleski | |
| 5,374,244 A | 12/1994 | Clement et al. | |
| 5,395,361 A | 3/1995 | Fox et al. | |
| 5,411,510 A | 5/1995 | Fugo | |
| 5,413,574 A | 5/1995 | Fugo | |
| 5,423,330 A | 6/1995 | Lee | |
| 5,423,841 A | 6/1995 | Kornefeld | |
| 5,439,474 A | 8/1995 | Li | |
| 5,466,234 A | 11/1995 | Loeb et al. | |
| 5,478,338 A | 12/1995 | Reynard | |
| 5,484,433 A | 1/1996 | Taylor et al. | |
| 5,486,165 A | 1/1996 | Stegmann | |
| 5,487,725 A | 1/1996 | Peyman | |
| 5,522,829 A | 6/1996 | Michalos | |
| 5,527,332 A | 6/1996 | Clement | |
| 5,562,692 A | 10/1996 | Bair | |
| 5,569,197 A | 10/1996 | Helmus et al. | |
| 5,569,280 A | 10/1996 | Kamerling | |
| 5,601,094 A | 2/1997 | Reiss | |
| 5,601,593 A | 2/1997 | Freitag | |
| 5,626,558 A | 5/1997 | Suson | |
| 5,630,827 A | 5/1997 | Vijfvinkel | |
| 5,651,783 A | 7/1997 | Reynard | |
| 5,662,670 A | 9/1997 | Michalos | |
| 5,669,923 A | 9/1997 | Gordon | |
| 5,670,161 A | 9/1997 | Healy et al. | |
| 5,683,592 A | 11/1997 | Bartholomew et al. | |
| 5,700,243 A | 12/1997 | Narciso, Jr. | |
| 5,716,363 A | 2/1998 | Josephberg | |
| 5,728,117 A | 3/1998 | Lash | |
| 5,733,297 A | 3/1998 | Wang | |
| 5,741,244 A | 4/1998 | Klaas | |
| 5,755,731 A | 5/1998 | Grinberg | |
| 5,766,171 A | 6/1998 | Silvestrini | |
| 5,792,166 A | 8/1998 | Gordon et al. | |
| 5,827,321 A | 10/1998 | Roubin et al. | |
| 5,860,994 A | 1/1999 | Yaacobi | |
| 5,868,697 A | 2/1999 | Richter et al. | |
| 5,873,883 A | 2/1999 | Cozean, Jr. et al. | |
| 5,888,201 A | 3/1999 | Stinson et al. | |
| 5,891,084 A | 4/1999 | Lee | |
| 5,893,862 A | 4/1999 | Pratt et al. | |
| 5,898,697 A | 4/1999 | Hurme et al. | |
| 5,921,999 A | 7/1999 | Dileo | |
| 5,925,056 A | 7/1999 | Thomas et al. | |
| 5,957,921 A | 9/1999 | Mirhashemi et al. | |
| 5,989,262 A | 11/1999 | Josephberg | |
| 6,036,688 A | 3/2000 | Edwards | |
| 6,059,792 A | 5/2000 | Josephberg | |
| 6,066,138 A | 5/2000 | Sheffer et al. | |
| 6,135,998 A | 10/2000 | Palanker | |
| 6,142,996 A * | 11/2000 | Mirhashemi et al. | 606/41 |
| 6,162,202 A | 12/2000 | Sicurelli et al. | |
| 6,165,190 A | 12/2000 | Nguyen | |
| 6,179,830 B1 | 1/2001 | Kokubu | |
| 6,203,518 B1 | 3/2001 | Anis et al. | |
| 6,217,598 B1 | 4/2001 | Berman et al. | |
| 6,241,721 B1 | 6/2001 | Cozean et al. | |
| 6,264,668 B1 | 7/2001 | Prywes | |
| 6,306,155 B1 | 10/2001 | Chandler et al. | |
| 6,379,370 B1 | 4/2002 | Feinsod | |
| 6,413,262 B2 | 7/2002 | Saishin et al. | |
| 6,440,103 B1 | 8/2002 | Hood et al. | |
| 6,503,263 B2 | 1/2003 | Adams | |
| 6,506,176 B1 | 1/2003 | Mittelstein et al. | |
| 6,544,254 B1 | 4/2003 | Bath | |
| 6,551,326 B1 | 4/2003 | Van Heugten et al. | |
| 6,575,929 B2 | 6/2003 | Sussman et al. | |
| 6,616,996 B1 | 9/2003 | Keith et al. | |
| 6,629,980 B1 | 10/2003 | Eibschitz-Tsimhoni | |
| 6,673,064 B1 | 1/2004 | Rentrop | |
| 6,764,439 B2 | 7/2004 | Schaaf et al. | |
| 6,979,328 B2 | 12/2005 | Baerveldt et al. | |
| 7,011,666 B2 | 3/2006 | Feinsod | |
| 7,135,009 B2 | 11/2006 | Tu et al. | |
| 7,729,779 B2 * | 6/2010 | Babaev | 607/115 |
| 2002/0007150 A1 | 1/2002 | Johnson | |
| 2002/0091402 A1 | 7/2002 | Feinsod | |
| 2002/0161365 A1 | 10/2002 | Martins | |
| 2004/0092982 A1 | 5/2004 | Sheffer | |
| 2004/0106929 A1 | 6/2004 | Masket | |
| 2004/0116950 A1 | 6/2004 | Eibschitz-Tsimhoni | |
| 2005/0054972 A1 | 3/2005 | Adams et al. | |
| 2005/0228419 A1 | 10/2005 | El-Mansoury | |
| 2006/0036270 A1 | 2/2006 | Terao | |
| 2006/0100617 A1 * | 5/2006 | Boukhny | 606/41 |
| 2006/0106370 A1 | 5/2006 | Baerveldt et al. | |
| 2006/0241580 A1 | 10/2006 | Mittelstein et al. | |
| 2006/0259053 A1 | 11/2006 | El-Mansoury | |
| 2007/0010812 A1 | 1/2007 | Mittelstein et al. | |
| 2007/0049957 A1 | 3/2007 | Benitez et al. | |
| 2007/0060926 A1 | 3/2007 | Escaf | |
| 2007/0073275 A1 | 3/2007 | Conston et al. | |
| 2007/0078359 A1 | 4/2007 | Luloh et al. | |
| 2007/0191862 A1 | 8/2007 | Ellis | |
| 2007/0239156 A1 | 10/2007 | Palanker et al. | |
| 2007/0276420 A1 | 11/2007 | Sorensen et al. | |
| 2008/0021446 A1 * | 1/2008 | Swanson | 606/41 |
| 2009/0216225 A1 | 8/2009 | Ben-Nun | |
| 2009/0287143 A1 | 11/2009 | Line | |
| 2009/0287233 A1 | 11/2009 | Huculak | |
| 2010/0057069 A1 | 3/2010 | Ben-Nun | |
| 2010/0094278 A1 | 4/2010 | Jia et al. | |
| 2010/0179544 A1 | 7/2010 | Boukhny et al. | |

FOREIGN PATENT DOCUMENTS

| | | |
|---|---|---|
| DE | 3205959 A1 | 9/1983 |
| DE | 3248101 A1 | 6/1984 |
| DE | 3434930 A1 | 4/1986 |
| DE | 8710541 U1 | 11/1987 |
| DE | 197 40 530 A1 | 3/1990 |
| DE | 4012882 A1 | 10/1991 |
| DE | 9311879 U1 | 11/1993 |
| DE | 19719549 A1 | 11/1998 |
| DE | 19809510 A1 | 9/1999 |
| DE | 10220253 A1 | 11/2002 |
| EP | 183385 B1 | 3/1989 |
| EP | 165657 B1 | 7/1989 |
| EP | 0335714 A2 | 10/1989 |
| EP | 358990 A1 | 3/1990 |
| EP | 0228185 B1 | 7/1990 |
| EP | 0355341 B1 | 10/1992 |
| EP | 0537116 A1 | 4/1993 |

| | | |
|---|---|---|
| EP | 506618 B1 | 7/1995 |
| EP | 0730848 A2 | 9/1996 |
| EP | 0730848 A3 | 7/1997 |
| EP | 0788802 A2 | 8/1997 |
| EP | 0898947 A2 | 3/1999 |
| EP | 0898947 A3 | 9/1999 |
| EP | 0730848 B1 | 4/2000 |
| EP | 0788802 A3 | 4/2000 |
| EP | 1010410 A1 | 6/2000 |
| EP | 0986328 A4 | 5/2001 |
| EP | 1095641 A1 | 5/2001 |
| EP | 0788802 B1 | 7/2006 |
| EP | 1809196 A4 | 3/2008 |
| ES | 2 103 635 | 9/1997 |
| FR | 2544979 A1 | 11/1984 |
| FR | 2588751 A1 | 4/1987 |
| FR | 2676355 | 11/1992 |
| FR | 2677244 A1 | 12/1992 |
| FR | 2702955 A1 | 9/1994 |
| FR | 2707872 A1 | 1/1995 |
| FR | 2830186 A1 | 4/2003 |
| FR | 2855745 A1 | 12/2004 |
| FR | 2855746 A1 | 12/2004 |
| FR | 2924924 A1 | 6/2009 |
| GB | 2247174 A | 2/1992 |
| GB | 2437252 A | 10/2007 |
| RU | 1790934 A1 | 1/1993 |
| RU | 1790935 A1 | 1/1993 |
| RU | 1148613 A1 | 4/1995 |
| SU | 452338 | 12/1974 |
| SU | 1301400 A1 | 4/1987 |
| SU | 1395314 A1 | 5/1988 |
| SU | 1431752 A1 | 10/1988 |
| SU | 1440496 A1 | 11/1988 |
| SU | 1766403 A1 | 10/1992 |
| WO | WO 86/02257 A1 | 4/1986 |
| WO | WO 93/01755 A1 | 2/1993 |
| WO | WO 93/20765 A1 | 10/1993 |
| WO | WO 95/08310 A1 | 3/1995 |
| WO | WO 96/06570 A1 | 3/1996 |
| WO | WO 97/26835 A1 | 7/1997 |
| WO | WO 97/30669 A1 | 8/1997 |
| WO | WO 98/49945 A1 | 11/1998 |
| WO | WO 99/60936 A1 | 12/1999 |
| WO | WO 00/48540 A1 | 8/2000 |
| WO | WO 01/56519 A1 | 8/2001 |
| WO | WO 01/60266 A1 | 8/2001 |
| WO | WO 03/022174 | 3/2003 |
| WO | WO 03/022174 A3 | 3/2003 |
| WO | WO 03/039335 A2 | 5/2003 |
| WO | WO 03/039335 A3 | 5/2003 |
| WO | WO 03/045290 A1 | 6/2003 |
| WO | WO 2004/039295 | 5/2004 |
| WO | WO 2004/071312 A1 | 8/2004 |
| WO | WO 2006/052374 A2 | 5/2006 |
| WO | WO 2006/052374 A3 | 5/2006 |
| WO | WO 2006/109255 A1 | 10/2006 |
| WO | WO 2006/109290 A2 | 10/2006 |
| WO | WO 2006/117772 A1 | 11/2006 |
| WO | WO 2007/121485 A2 | 10/2007 |
| WO | WO 2008/080149 A1 | 7/2008 |
| WO | WO 2009/140414 A1 | 11/2009 |
| WO | WO 2009/153550 A1 | 12/2009 |
| WO | WO 2010/044988 A1 | 4/2010 |
| WO | WO 2010/068662 A1 | 6/2010 |
| WO | WO 2010/080859 A1 | 7/2010 |
| WO | WO 2010/141179 A1 | 12/2010 |
| WO | WO 2010/141181 A1 | 12/2010 |
| WO | WO 2011/102928 A1 | 8/2011 |

OTHER PUBLICATIONS

Sussman, Glen et al., Capsularhexis Device with Flexible Heating Element having an Angled Transitional Neck, U.S. Appl. No. 12/477,175, filed Jun. 3, 2009, 32 pages.

International Searching Authority, International Preliminary Report on Patentability, PCT/US2005/036670, May 15, 2007, 4 pages.

Huculak, John C. et al., Capsularhexis Device Using Pulsed Electric Fields, U.S. Appl. No. 12/618,805, filed Nov. 16, 2009, 14 pages.

Jia, Guangyao, et al., Capsule Polishing Device and Method for Capsule Polishing, U.S. Appl. No. 12/777,820, filed May 11, 2010, 26 pages.

Jia, Guangyao, et al., Capsulotomy Repair Device and Method for Capsulotomy Repair, U.S. Appl. No. 12/754,119, filed Apr. 5, 2010, 40 pages.

Karmel, Miriam, "Glaucoma Surgies: Trabectome and Canaloplasty Take the Stage," publication, May 2009, pp. 29-30, American Academy of Ophthalmology.

Lewandowski, Julia T., "Improving Ab Interno Trabeculotomy, A combination of advanced technology and insightful design may prompt surgeons to adopt a new technique for lowering IOP," article, Jul. 2007, 4 pages, Bryn Mawr Communications.

Abstract of SU1805938; Publication date Mar. 30, 1993; Priority date Mar. 11, 1991.

Sussman, Glenn, et al., Small Gauge Ablation Probe for Glaucoma Surgery, U.S. Appl. No. 12/707,747, filed Feb. 18, 2010, 11 pages.

International Searching Authority, International Search Report, PCT/US2010/020295, May 17, 2010, 4 pages.

International Searching Authority, Written Opinion of the International Searching Authority, PCT/US2010/020295, May 17, 2010, 8 pages.

International Searching Authority, International Search Report, PCT/US2009/067305, Apr. 13, 2010, 4 pages.

International Searching Authority, Written Opinion of the International Searching Authority, PCT/US2009/067305, Apr. 13, 2010, 6 pages.

International Searching Authority, Written Opinion of the International Searching Authority, International Application No. PCT/US2011/021608, Mar. 1, 2011, 9 pages.

International Searching Authority, International Search Report, International Application No. PCT/US2011/021608, Mar. 1, 2011, 6 pages.

* cited by examiner

FLEXIBLE, AUTOMATED CAPSULORHEXIS DEVICE

TECHNICAL FIELD

The present invention relates generally to the field of cataract surgery and more particularly to methods and apparatus for performing a capsulorhexis.

BACKGROUND

An accepted treatment for the treatment of cataracts is surgical removal of the lens and replacement of the lens function by an artificial intraocular lens (IOL). In the United States, the majority of cataractous lenses are removed by a surgical technique called phacoemulsification. Prior to removing the cataractous lens, an opening, or rhexis, must be made in the anterior capsule. During phacoemulsification, there is a great deal of tension on the cut edges of the anterior capsulorhexis while the lens nucleus is emulsified. Accordingly, a continuous cut or tear (rhexis), without "tags," is a critical step in a safe and effective phacoemulsification procedure.

If the capsule is opened with numerous small capsular tears, the small tags that remain can lead to radial capsular tears which may extend into the posterior capsule. Such a radial tear constitutes a complication since it destabilizes the lens for further cataract removal and safe intraocular lens placement within the lens capsule later in the operation. Further, if the posterior capsule is punctured then the vitreous may gain access to the anterior chamber of the eye. If this happens, the vitreous must be removed by an additional procedure with special instruments. The loss of vitreous is also associated with an increased rate of subsequent retinal detachment and/or infection within the eye. Importantly, these complications are potentially blinding.

Conventional equipment used for phacoemulsification includes an ultrasonically driven handpiece with an attached cutting tip. In some of these handpieces, the operative part is a centrally located, hollow resonating bar or horn directly attached to a set of piezoelectric crystals. The crystals supply ultrasonic vibration for driving both the horn and the attached cutting tip during phacoemulsification.

Prior art devices and methods used for the capsulorhexis procedure require a great deal of skill on the part of the surgeon to produce a continuous curvilinear capsular opening. This is due to the extreme difficulty in controlling the path of the cutting tip of the device. For example, a typical procedure begins with a capsular incision made with a cystotome, e.g., a cutting tip as described above. This incision is then coaxed into a circular or oval shape by pushing the leading edge of the incision in the capsule, using the cystotome as a wedge rather than in a cutting fashion. Alternatively, the initial capsular incision may be torn into a circular shape by grasping the leading edge with fine caliber forceps and advancing the cut. Either of these approaches involves a very challenging maneuver and the tearing motion can sometimes lead to an undesirable tear of the capsule toward the back of the lens, even in the most experienced hands.

Moreover, even if a smooth capsular opening without tags is ultimately produced, the size and/or position of the capsular opening may present a problem. For instance, a capsular opening that is too small can impede the safe removal of the lens nucleus and cortex and prevent proper intraocular lens insertion into the lens capsule. The additional stresses necessary to accomplish the operation with a small or misplaced capsular opening put the eye at risk for zonular and capsular breakage. Either of these complications will likely increase the length and complexity of the operation and may result in vitreous loss.

A continuous, properly positioned, and circular opening is thus highly desirable because it results in: (1) a significant reduction in radial tears and tags within the anterior capsule, (2) capsule integrity necessary for proper centering of a lens prosthesis; (3) safe and effective hydrodissection; and (4) safe use of capsular procedures on patients having poorly visualized capsules and/or small pupil openings. In addition, the capsulorhexis should be properly dimensioned relative to the diameter of the IOL being implanted in order to reduce the chances of a secondary cataract, also called posterior capsule opacification ("PCO") and for use with proposed accommodative IOLs designs. Therefore, there is a continuing need for an improved device for performing an anterior chamber capsulorhexis.

SUMMARY

As described more fully below, embodiments of the present invention include a flexible capsulorhexis electrode device comprising an elastomeric ring with bipolar electrodes disposed upon the ring's front surface. The flexible electrode device is removably attachable to an insertion tool via mating connectors on the electrode device and on stretcher bars of the insertion tool. The stretcher bars are configured so that one of the stretcher bars may be translated relative to the other, stretching the flexible electrode device into an elongated configuration. In its elongated configuration, the flexible electrode device may be inserted into the anterior chamber of an eye through a small incision. After insertion into the eye, the flexible electrode device is permitted to relax into its normal, generally circular, shape, and applied to the lens capsule. The electrodes are energized, using a high-frequency power source, to cauterize a circular section of the anterior lens capsule, thus weakening the capsule tissue and defining a portion of the lens capsule that can be easily removed with forceps. After the cauterization process, the electrode device is stretched into its elongated position before removal from the eye.

Aspects of the present invention include the flexible capsularhexis electrode device and insertion tool described above, and variants thereof, as well as corresponding methods for using an autocapsulorhexis system. Accordingly, embodiments of the present invention include a capsulorhexis electrode device, comprising an elastomeric ring, first and second electrically conductive traces disposed at a first face of the elastomeric ring and extending concentrically around the elastomeric ring, and first and second electrically conductive connectors. The first and second electrically conductive connectors are electrically connected to the first and second traces, respectively, and are disposed at opposing points across the elastomeric ring from one another. In some embodiments, at least one of the first and second electrically conductive connectors comprises a socket disposed in the elastomeric ring; said socket is accessible to a mating connector from a direction opposite the first face in some of these embodiments. In other embodiments, at least one of the first and second electrically conductive connectors comprises a pin attached to and extending from the elastomeric ring; said pin extends from the elastomeric ring in a direction substantially opposite the first face in some of these embodiments. In various embodiments, one or both of the first and second electrically conductive traces comprises electrically conductive ink applied to the first face of the elastomeric ring or adhesive strips applied to the first face of the elastomeric ring.

In several embodiments, the first trace extends completely around the elastomeric ring; in some of these embodiments the second trace extends completely around the elastomeric ring except for a discontinuity adjacent to an electrical connection between the first trace and the first electrically conductive connector.

Other embodiments of the invention include an autocapsulorhexis system, comprising a handpiece, a first stretcher bar fixed to the handpiece and extending from a distal end of the handpiece, and a second stretcher bar extending from the distal end of the handpiece and attached to the handpiece so as to allow the second stretcher bar to reciprocate relative to the first stretcher bar. In these embodiments, each of the first and second stretcher bars comprises an electrically conductive connector configured to mate with a corresponding connector on a removable, flexible, capsulorhexis electrode device.

In some of these embodiments, at least one of the electrically conductive connectors comprises a pin configured to mate with a corresponding socket on the capsulorhexis electrode device. In others, at least one of the electrically conductive connectors comprises a socket configured to mate with a corresponding pin on the capsulorhexis electrode device. In a few embodiments, the second stretcher bar may be mounted to a thumb slide on the handpiece device, for manual operation by the system's user, while other systems may include an electric drive system for translating the second stretcher bar. Other embodiments of the present invention include any of the autocapsulorhexis systems described herein, with a removable, flexible, capsulorhexis electrode device installed thereupon, so that the electrically conductive connectors on the first and second bars are engaged with the corresponding connectors on the capsulorhexis electrode device.

Of course, those skilled in the art will appreciate that the present invention is not limited to the above features, advantages, contexts or examples, and will recognize additional features and advantages upon reading the following detailed description and upon viewing the accompanying drawings.

DETAILED DESCRIPTION

Figure 1A:
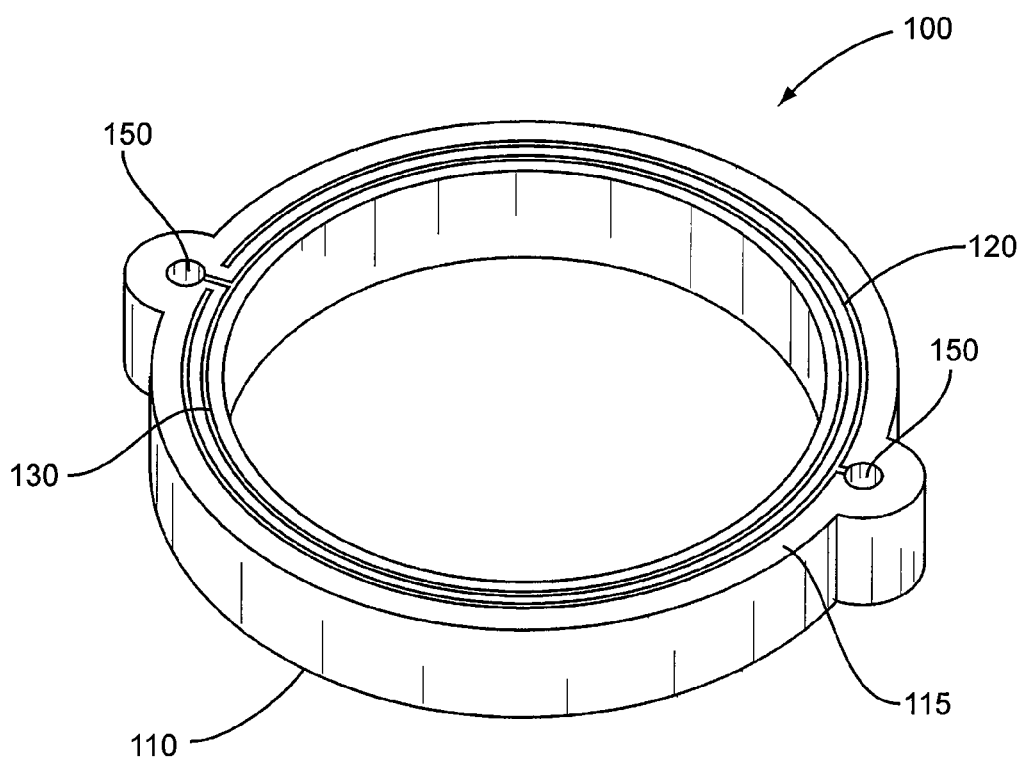
FIG. 1A is a first view of an exemplary capsulorhexis electrode device according to some embodiments of the present invention.

Various embodiments of the present invention provide apparatus and corresponding methods of use for performing capsulorhexis. In particular, the present invention relates to a surgical instrument, a flexible capsulorhexis electrode device, which may be positioned within the anterior chamber of an eye through a small incision to perform capsulorhexis, or capsulotomy. This procedure facilitates phacoemulsification of a cataractous lens and insertion of an artificial intraocular lens (IOL).

Various methods and devices for automating the capsularhexis process have been proposed. United States Patent Application Publication No. 2006/0100617, the entire contents of which are incorporated herein by reference, describes an "autocapsulorhexis" device comprising a circular, flexible ring made of an elastomer or an acrylic or thermoplastic material. Embedded within each of various embodiments of this flexible ring is either a resistance-heating element or a pair of bipolar electrodes, which are energized according to known techniques to produce localized heating on the anterior capsule, so as to define a weakened boundary for an easy detachment of the portion of the capsule within the circular ring. Various other devices have been proposed, many of which depend on resistive-heating cautery elements, such as U.S. Pat. No. 6,066,138, issued May 23, 2000; U.S. Pat. No. 4,481,948, issued Nov. 13, 1984; and WIPO Publication No. WO 2006/109290 A2, published Oct. 19, 2006. The entire contents of each of the previous references are incorporated by reference herein, for the purpose of providing background and context for the present invention.

Although those skilled in the art will appreciate the broader applicability of several of the inventive techniques and apparatus disclosed herein, the present invention is generally directed to methods and apparatus for performing capsulorhexis using high-frequency electrical current applied to the anterior lens capsule through a pair of bipolar electrodes. One approach to fabricate such types of electrodes is to form the electrodes by depositing electrically conductive ink onto an elastomeric ring to form conductive traces, e.g., by insert molding the elastomeric substrate and then screen-printing conductive traces to the desired dimensions. Alternatively, an adhesive trace can be applied to a pre-fabricated elastomeric ring, or conductive traces can be combined with the elastomeric ring 110 through an insert molding process. FIG. 1 thus illustrates an exemplary capsulorhexis electrode device 100, according to some embodiments of the present invention, comprising a flexible, elastomeric ring 110 with bipolar electrodes 120 and 130 formed on a front face 115 of the ring.

The elastomeric ring 110 and the electrodes 120 and 130 are dimensioned according to the desired size of the capsulotomy, e.g., with a diameter of approximately 5 millimeters. Those skilled in the art will appreciate that a circular opening is preferred, to avoid tearing when the portion of the lens capsule within the opening is removed. Accordingly, the elastomeric ring 110 of FIG. 1 and the electrodes 120 and 130 thereupon are illustrated as circular. Of course, those skilled in the art will appreciate that some variation from a circular shape may be acceptable in some applications. Thus, the term "ring" as used herein will be understood to include generally circular, oval, or elliptical structures.

The electrodes 120 and 130 define the boundaries of the portion of the lens capsule that is cauterized by the high-frequency current when the electrodes are energized. When applied against the anterior lens capsule, the spacing between the electrodes 120 and 130 defines a gap across which the high-frequency current flows when the electrodes are energized. The basic principles of such electro-surgery, which may involve, for example, frequencies of greater than 100 kHz, are well known to those skilled to the art. Accordingly, the details of such procedures, which are not necessary to a complete understanding of the present invention, are not provided herein.

In the exemplary configuration illustrated in FIGS. 1A, the inner electrode 130 forms a complete circle around the face of the elastomeric ring 110. The outer electrode 120 is concentric to electrode 130, and forms a circle except for a small gap. In the pictured configuration, this discontinuity, which is near a connection point to electrode 130, is necessary to maintain electrical isolation between the electrodes.

Figure 1B:
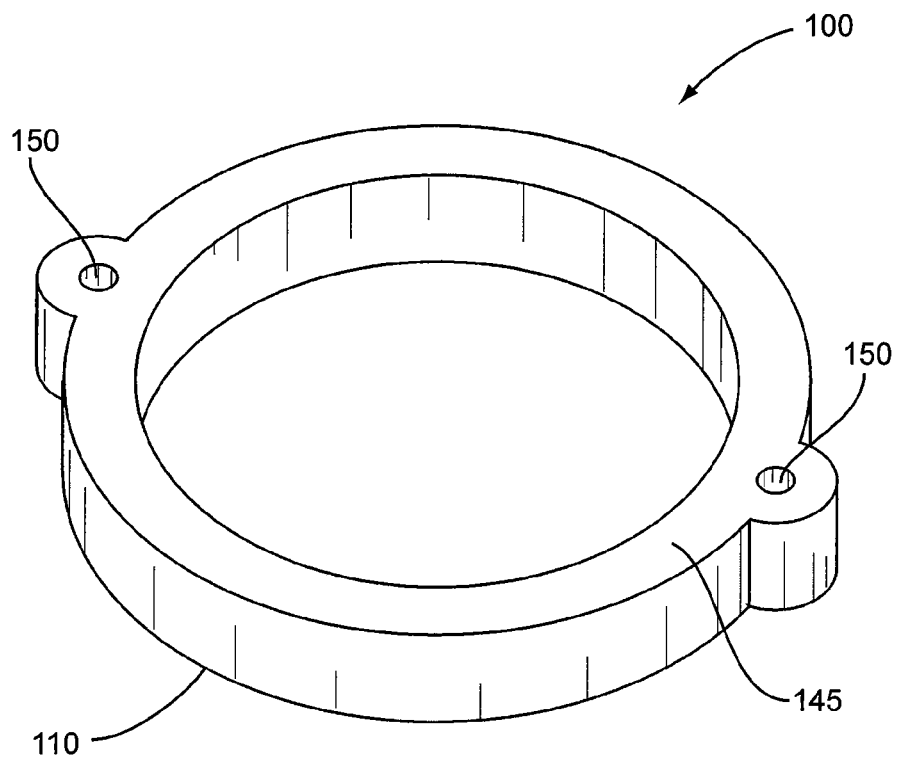
FIG. 1B is a second view of the capsulorhexis electrode device of FIG. 1A, illustrating the reverse face of the device.

FIG. 1B illustrates the reverse side of the capsulorhexis electrode device 100. As will be explained in more detail below, connectors 150 provide mechanical attachment points between the flexible capsulorhexis electrode device 100 and an insertion tool. Connectors 150 also provide electrical connections between the electrodes 120 and 130 and corresponding electrodes on the insertion tool. In FIG. 1B, connectors 150 are illustrated as sockets, extending all the way through the elastomeric ring 110. In some embodiments, these sockets may simply comprise electrically conductive ink applied on the inner surface of a hole formed through the elastomeric ring 110. In others, the sockets may be formed from electrically conductive grommets inserted into the holes, or as rigid sockets insert molded into the elastomeric ring 110. In any case, each of the two connectors 150 is electrically connected to corresponding ones of the electrodes 120 and 130 via, e.g., electrically conductive ink, adhesive electrical traces, solder, or the like, and also provides an electrically conductive contact surface for a corresponding connector on an insertion tool.

Figure 2:
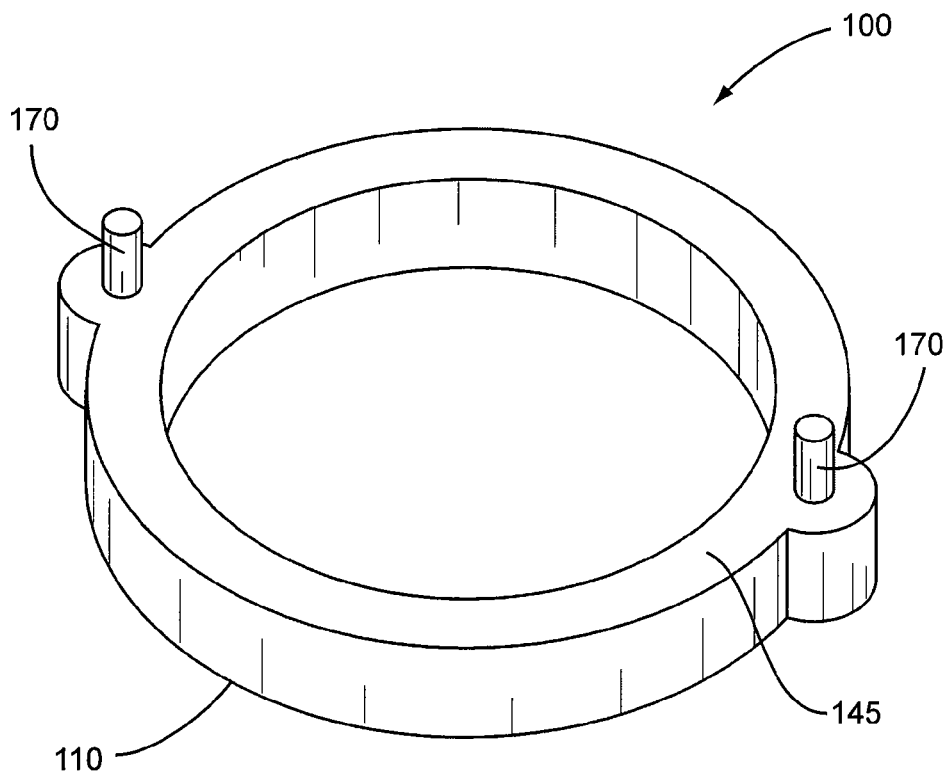
FIG. 2 illustrates an alternative embodiment of the capsularhexis electrode device of FIGS. 1A and 1B.

In an alternate embodiment, such as the embodiment pictured in FIG. 2, each of the connectors comprises a pin 170 extending from the rear face 145 of the elastomeric ring. The outer surface of pins 170 comprises an electrically conductive material, for making contact with a corresponding socket on an insertion tool, and each pin is connected to a corresponding one of electrodes 120 and 130 via, e.g., any of the means described above.

Figure 3:
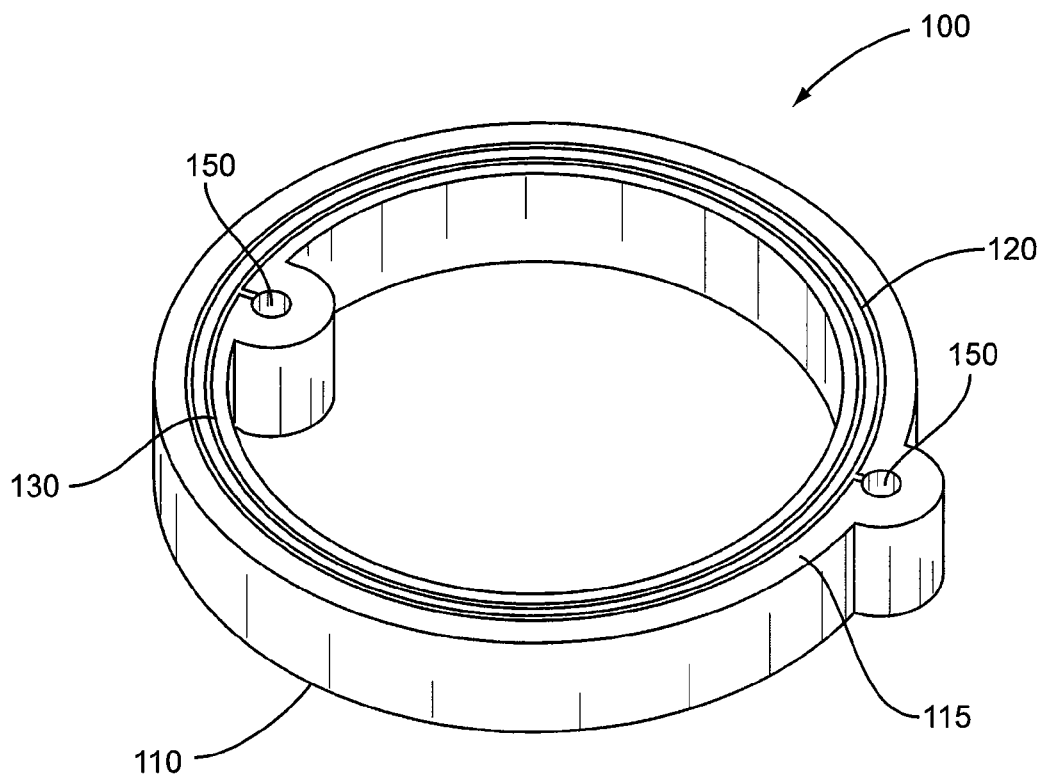
FIG. 3 illustrates still another alternative embodiment of a capsularhexis electrode device.

However, those skilled in the art will appreciate that other configurations are possible. For instance, in the configuration pictured in FIGS. 1 and 2, the connectors 150 are disposed at directly opposing points across the elastomeric ring 110 from one another, and are both outside the concentric circles formed by electrodes 120 and 130, necessitating the small discontinuity in electrode 120 adjacent to the point where electrode 130 connects to one of the connectors 150. In other configurations, one or both of the connectors may instead be positioned inside the concentric circles formed by electrodes 120 and 130. If one connector is disposed towards the interior of the ring and the other towards the exterior, both of the electrodes 120 and 130 may form a complete loop. An exemplary capsulorhexis device according to this configuration is shown in FIG. 3. Those skilled in the art will recognize, however, that the embodiment pictured in FIG. 3 will have a somewhat larger insertion profile than the embodiments pictured in FIGS. 1 and 2, assuming that the devices are similarly dimensioned.

Those skilled in the art will also appreciate that designations herein of a "front face" and a "rear face" are arbitrary, and adopted only for the sake of convenience. Unless specified otherwise, the term "front face" refers to the surface upon which the electrodes 120 and 130 are formed, while "rear face" refers to the opposite surface. Those skilled in the art will also appreciate that either or both of front face 115 and 145, or any of the flat surfaces, may be curved. In some embodiments, for example, the front face 115 may have a slightly convex curve, rather than a flat surface. On the other hand, the reverse side of electrode device 100 might have a concave curve, in some cases to the extent that the inner, outer, and reverse surfaces of the device 100 form a single curved contour.

Figure 4:
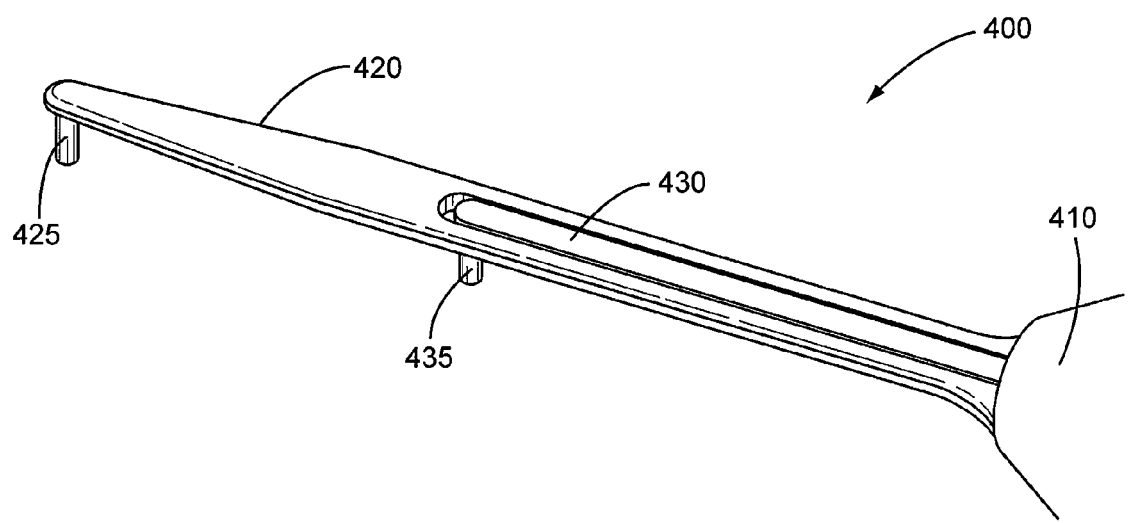
FIG. 4 illustrates a capsulorhexis insertion device according to some embodiments of the present invention.
Figure 5:
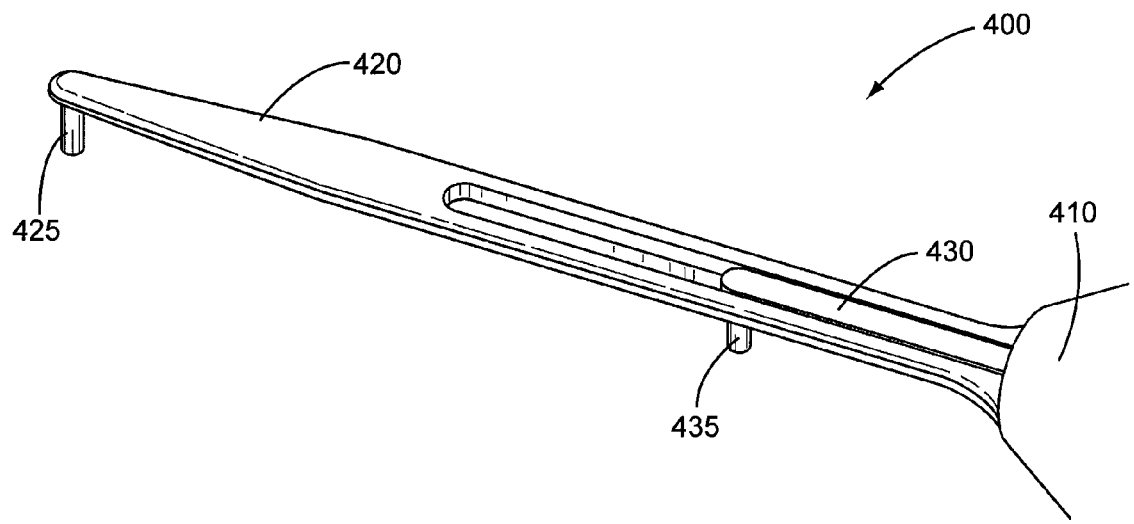
FIG. 5 illustrates the capsulorhexis insertion device of FIG. 4 in a stretching configuration.

The female connectors 150 or the male connectors 170 may be used to facilitate "folding" of the elastomeric capsulorhexis electrode device 100 by stretching it into a shape that can be inserted into an eye through a very small incision, e.g., through a 2 millimeter incision. This mechanical stretching of the capsulorhexis electrode device 100 can be achieved with an insertion tool such as the one pictured in FIGS. 4, 5, 6, and 7. Insertion tool 400 includes a handpiece 410, a first stretcher bar 420, and a second stretcher bar 430. The first and second stretcher bars 420 and 430 have electrically conductive connectors 425 and 435, respectively, which are configured for mechanical and electrical connection to corresponding connectors on a flexible capsulorhexis electrode device. In the pictured embodiment, the first stretcher bar 420 is rigidly fastened to the handpiece 420, while the second stretcher bar 430 can be translated from an extended position, as shown in FIG. 4, to a retracted position, as shown in FIG. 5. This translation may be under the manual control of an operator, such as via a thumb slide (not shown) disposed on the handpiece 410, in some embodiments. In other embodiments, the second stretcher bar 430 may be translated using a motorized drive system, using any of a variety of miniature linear actuators.

Figure 6:
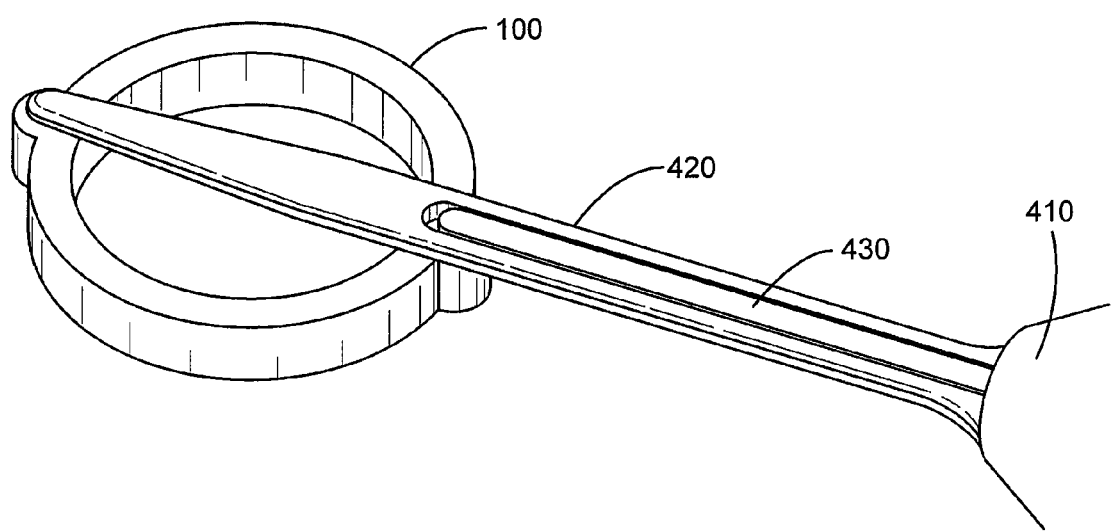
FIG. 6 illustrates the capsulorhexis insertion device of FIG. 4 with an exemplary capsulorhexis electrode device installed thereupon.

As shown in FIG. 6, a flexible capsulorhexis electrode device 100 may be installed onto the connectors 425 and 435, with the second stretcher bar 430 in its extended position. The electrode device 100 is installed onto the connectors 425 and 435 so that the electrodes 120 and 130 are facing away from the tool.

Figure 7:
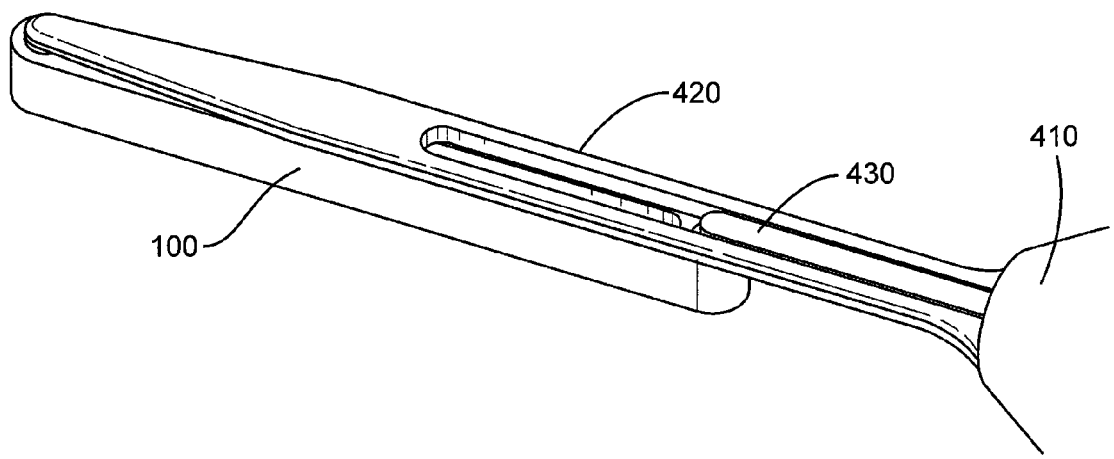
FIG. 7 illustrates the capsulorhexis insertion system of FIG. 6 in a stretching configuration.

Linear translation of the second stretcher bar 430 to its retracted position stretches the electrode device 100 so that it may be inserted into the eye through an incision that is considerably smaller than the maximum dimension of the electrode device in its "relaxed" configuration. FIG. 7 illustrates the flexible electrode device 100 in its stretched configuration. After insertion into the eye, the second stretcher bar 430 may be translated into its extended position again, permitting the flexible electrode device 100 to return to its generally circular shape for the capsulorhexis procedure.

The particular insertion tool 400 pictured in FIGS. 4-7 comprises mating connectors 425 and 435 in the form of pins, suitable for mechanical and electrical mating with the female (socket) connectors 150 of FIGS. 1A and 1B. Those skilled in the art will appreciate, however, that different mating connectors 425 and 435 suitable for mating with male connectors 170 (as shown in FIG. 2) may be used in alternate embodiments. Thus, for example, connectors 425 and 435 may each comprise a post, in some embodiments, extending from respective stretcher bars, with a socket disposed in each for mechanical and electrical engagement with the male connectors 170. Other embodiments may employ one female connector and one male connector, for mating with a suitably designed electrode device. In any case, the connectors 425 and 435 comprise an electrically conductive surface that contacts the corresponding connector on the electrode device. This electrically conductive surface provides an electrical attachment to supply wires or leads, which may extend through the respective stretcher bars 420 and 430, through the handpiece 410, and to an appropriate power source. As noted above, this power source provides a high-frequency current to the anterior lens capsule when the device is positioned within the eye and energized.

Figure 8:
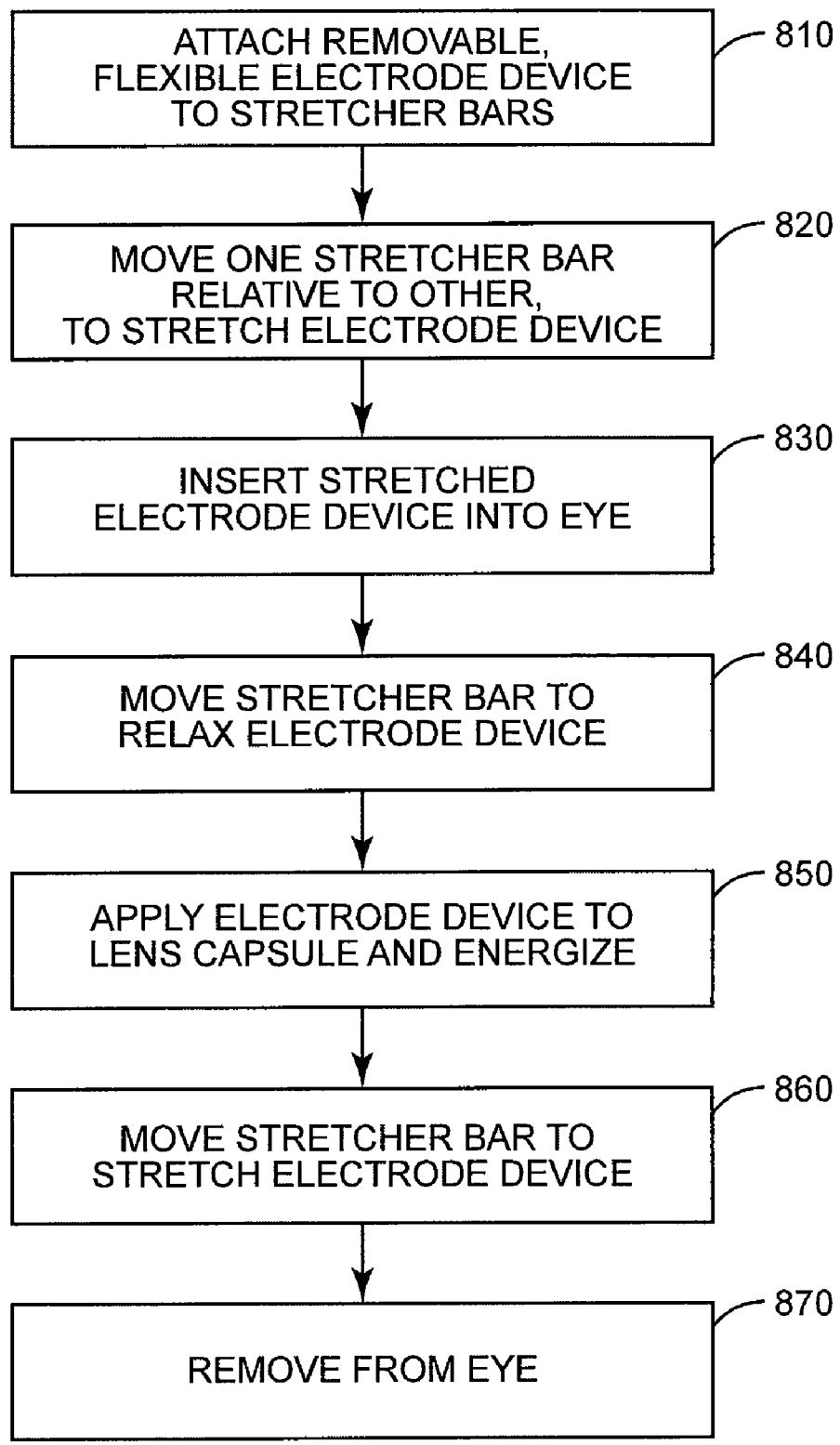
FIG. 8 is a process flow diagram illustrating an exemplary method for using an autocapsulorhexis system.

With the above-described device configurations in mind, those skilled in the art will appreciate that FIG. 8 illustrates an exemplary method for utilizing an autocapsulorhexis system according to some embodiments of the present invention. The illustrated method begins, as shown at block 810, with the attachment of a removable, flexible electrode device to first and second stretcher bars of an insertion tool, e.g., as shown in FIG. 6. The electrode device is readily assembled to and removed from the tool and may in some embodiments be disposable. Those skilled in the art will appreciate that this approach allows the insertion tool (which includes the stretcher bars and the mating connectors) to be sterilized and reused multiple times.

In any event, the illustrated procedure continues, as shown at block 820, with translation of one stretcher bar, relative to the other, so that the flexible electrode device is stretched into an elongated configuration for insertion into the anterior chamber of a patient's eye. After insertion into the eye, as shown at block 830, the stretcher bar is returned to the extended position, as shown at block 840, thus allowing the flexible electrode device to relax to its normal shape. The front face of the electrode device is placed against the anterior lens capsule, so that the bipolar electrodes are in contact with or in close proximity to the capsule, and the device energized, as shown at block 850. After energizing the device, the capsule area defined by the electrodes is weakened and subject to easy removal using conventional forceps.

After the device is energized, the stretcher bar is translated once more, as shown at block 860, to once again stretch the flexible electrode device into its elongated position. The device may then be easily removed from the anterior chamber of the eye, as shown at block 870.

The preceding descriptions of various embodiments of a flexible capsulorhexis electrode device, an autocapsulorhexis insertion tool, and methods for utilizing these devices, were given for purposes of illustration and example. Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A capsulorhexis electrode device, comprising:
an elastomeric ring;
first and second electrically conductive traces disposed at a first face of the elastomeric ring and extending concentrically around the elastomeric ring;
a first electrically conductive connector, electrically connected to the first trace; and
a second electrically conductive connector electrically connected to the second trace and disposed at an opposing point across the elastomeric ring from the first electrically conductive connector;
wherein at least one of the first and second electrically conductive connectors comprises a socket disposed in the elastomeric ring;
wherein said socket is accessible to a mating connector from a direction opposite the first face.

2. The capsulorhexis electrode device of claim 1, wherein at least one of the first and second electrically conductive traces comprises electrically conductive ink applied to the first face of the elastomeric ring.

3. The capsulorhexis electrode device of claim 1, wherein at least one of the first and second electrically conductive traces comprises adhesive strips applied to the first face of the elastomeric ring.

4. The capsulorhexis electrode device of claim 1, wherein the first trace extends completely around the elastomeric ring.

5. The capsulorhexis electrode device of claim 4, wherein the second trace extends completely around the elastomeric ring except for a discontinuity adjacent to an electrical connection between the first trace and the first electrically conductive connector.

6. The capsulorhexis electrode device of claim 1, wherein both the first and second electrically conductive connectors comprise a socket disposed in the elastomeric ring and wherein both sockets are accessible to corresponding mating connectors.

7. The capsulorhexis electrode device of claim 6, wherein the elastomeric ring is configured to be elongated when the sockets are engaged by the corresponding mating connectors and a distance between the corresponding mating connectors is increased.

8. A capsulorhexis electrode device, comprising:
an elastomeric ring;
first and second electrically conductive traces disposed at a first face of the elastomeric ring and extending concentrically around the elastomeric ring;
a first electrically conductive connector, electrically connected to the first trace; and
a second electrically conductive connector electrically connected to the second trace and disposed at an opposing point across the elastomeric ring from the first electrically conductive connector;
wherein at least one of the first and second electrically conductive connectors comprises a pin attached to and extending from the elastomeric ring;
wherein the pin extends from the elastomeric ring in a direction substantially opposite the first face.

9. The capsulorhexis electrode device of claim 8, wherein at least one of the first and second electrically conductive traces comprises electrically conductive ink applied to the first face of the elastomeric ring.

10. The capsulorhexis electrode device of claim 8, wherein at least one of the first and second electrically conductive traces comprises adhesive strips applied to the first face of the elastomeric ring.

11. The capsulorhexis electrode device of claim 8, wherein the first trace extends completely around the elastomeric ring.

12. The capsulorhexis electrode device of claim 11, wherein the second trace extends completely around the elastomeric ring except for a discontinuity adjacent to an electrical connection between the first trace and the first electrically conductive connector.

13. The capsulorhexis electrode device of claim 8, wherein both the first and second electrically conductive connectors comprise a pin attached to and extending from the elastomeric ring and wherein both pins are accessible to corresponding mating sockets on an insertion tool.

14. The capsulorhexis electrode device of claim 13, wherein the elastomeric ring is configured to be elongated when the pins are engaged by the corresponding mating sockets and a distance between the corresponding mating sockets is increased.

* * * * *